US010787420B2

(12) United States Patent
Liu et al.

(10) Patent No.: US 10,787,420 B2
(45) Date of Patent: Sep. 29, 2020

(54) BENZIMIDAZOLE COMPOUND AND PREPARATION METHOD THEREOF

(71) Applicants: SHANGDONG ENGINEERING AND TECHNOLOGY INSTITUTE OF LUNAN COAL CHEMICAL ENGINEERING, Zaozhuang (CN); ZAOZHUANG UNIVERSITY, Zaozhuang (CN); SHANDONG JITIAN AROMA CHEMICAL CO.LTD, Zaozhuang (CN); Asset (Suzhou) Pharma Co., Ltd., Suzhou (CN)

(72) Inventors: Xuejing Liu, Zaozhuang (CN); Ying Han, Zaozhuang (CN); Liang Yang, Zaozhuang (CN)

(73) Assignees: SHANDONG ENGINEERING AND TECHNOLOGY INSTITUTE OF LUNAN COAL CHEMICAL ENGINEERING, Zaozhuang (CN); ZAOZHUANG UNIVERSITY, Zaozhuang (CN); SHANDONG JITIAN AROMA CHEMICAL CO LTD, Zaozhuang (CN); Asset (Suzhou) Pharma Co., Ltd., Suzhou (CN)

( * ) Notice: Subject to any disclaimer, the term of this patent is extended or adjusted under 35 U.S.C. 154(b) by 0 days.

(21) Appl. No.: 16/485,457

(22) PCT Filed: Sep. 28, 2017

(86) PCT No.: PCT/CN2017/103942
§ 371 (c)(1),
(2) Date: Aug. 13, 2019

(87) PCT Pub. No.: WO2019/015112
PCT Pub. Date: Jan. 24, 2019

(65) Prior Publication Data
US 2020/0002291 A1    Jan. 2, 2020

(30) Foreign Application Priority Data

Jul. 19, 2017    (CN) .......................... 2017 1 0589775

(51) Int. Cl.
C07D 235/08    (2006.01)
C07D 405/06    (2006.01)
C07D 403/06    (2006.01)

(52) U.S. Cl.
CPC ......... *C07D 235/08* (2013.01); *C07D 403/06* (2013.01); *C07D 405/06* (2013.01)

(58) Field of Classification Search
CPC .. C07D 235/08; C07D 235/10; C07D 235/14; C07D 235/16
See application file for complete search history.

(56) References Cited

U.S. PATENT DOCUMENTS 5,801,180 A * 9/1998 Takase ................. C07D 239/84
514/266.24

FOREIGN PATENT DOCUMENTS

| CN | 106866545 A | * | 6/2017 | |
| CN | 106866545 A | | 6/2017 | |
| CN | 106946862 A | * | 7/2017 | |
| WO | WO-2016057834 A1 | * | 4/2016 | ............. A61K 45/06 |

OTHER PUBLICATIONS

B. Feitelson et al., Journal of the Chemical Society, 2389-2398 (1952) (Year: 1952).*
CAS Abstract of Journal of the Chemical Society, 2389-2398 (1952) (Year: 1952).*
CAS Abstract CN 106866545 (2017) (Year: 2017).*
CAS Abstract CN 106946862 (2017) (Year: 2017).*
English Language Machine Translation of CN 106866545 (2017) (Year: 2017).*
English Language Machine Translation of CN 106946862 (2017) (Year: 2017).*
D. Latham et al., Journal of the Chemical Society, Chemical Communications, 41-42 (1973) (Year: 1973).*
Y-C Chi et al., Synlett, 591-594 (2000) (Year: 2000).*

* cited by examiner

*Primary Examiner* — Mark L Shibuya
*Assistant Examiner* — Ebenezer O Sackey
(74) *Attorney, Agent, or Firm* — Bayramoglu Law Offices LLC

(57) ABSTRACT

A benzimidazole compound and a preparation method thereof. Various substituted benzimidazoles are synthesized by a $S_N2$ reaction and a cyclization reaction. Namely, o-fluorinated aryl-N,N-dimethyl-formamidine and primary amine are subjected to an cyclization by a one-pot reaction, wherein a fluorine atom is substituted by an amino, and then dimethylamine is eliminated, thus forming the product. The method does not require the use of any metal catalyst and/or any toxic reagent, and has a specific selectivity. No isomer exists in the reaction product.

5 Claims, No Drawings

BENZIMIDAZOLE COMPOUND AND PREPARATION METHOD THEREOF

CROSS REFERENCE TO THE RELATED APPLICATIONS

This application is the national phase entry of International Application No. PCT/CN2017/103942, filed on Sep. 28, 2017, which is based upon and claims priority to Chinese Patent Application No. 201710589775.0, filed on Jul. 19, 2017, the entire contents of which are incorporated herein by reference.

TECHNICAL FIELD

The present invention belongs to the technical field of organic synthesis, and relates to a benzimidazole compound and a preparation method thereof.

BACKGROUND

The benzimidazole ring system is one of the most common core structures used for drug discovery, and has been found in many biologically active compounds. For example, Raf (kinase inhibitor), LCK (lymphocyte-specific kinase inhibitor, etc.), 5-serotonin receptor, phosphodiacetate IV antihistamine Astemizole 4 and anti-ulcer omeprazole.

Researchers have made many efforts to develop and prepare the benzimidazole compounds. At present, there are three main methods for synthesizing 1-substituted benzimidazole derivatives.

(a) Route 1: a condensation reaction is performed on 1,2-diaminoarene 1 and formic acid to form benzimidazole core 2, and then N-alkylated is directly performed on a nitrogen of the benzimidazole ring to generate two regioisomers 3 and 4. However, in most cases, regioselective alkylation on a given nitrogen is difficult, resulting in a mixture of two regioisomers 3 and 4 (having a ratio of approximately 1:1) in the synthetic product of Route 1. The separation and characterization of the mixture is carried out by high-performance liquid chromatography (HPLC) and two-dimensional nuclear magnetic resonance (2D NMR) techniques, which is a time consuming and laborious process.

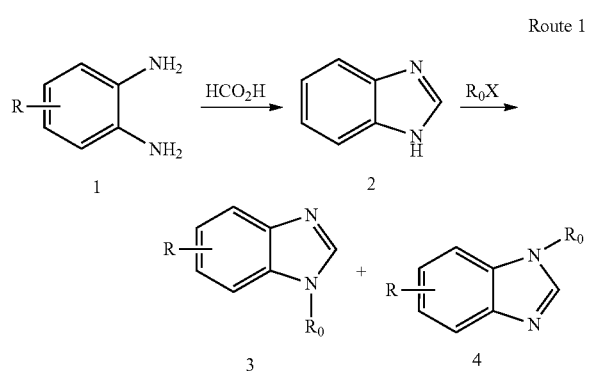

(b) Route 2: Alkylation of 2-nitroaniline 5 is performed, nitro group is reduced to amino group, and then cyclization is performed on 7 and formic acid to form desired compound 3.

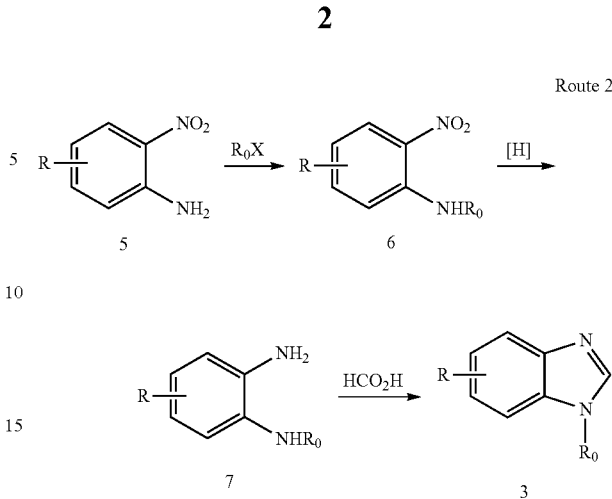

(c) Route 3: O-fluoronitrobenzene compound 8 is another precursor which is used to produce compound 3 by a three-step synthesis. The fluorine group of compound 8 is substituted by a primary amine ($S_N2$ reaction), the nitro group is reduced to an amine, and then the target compound is generated by cyclization of formic acid.

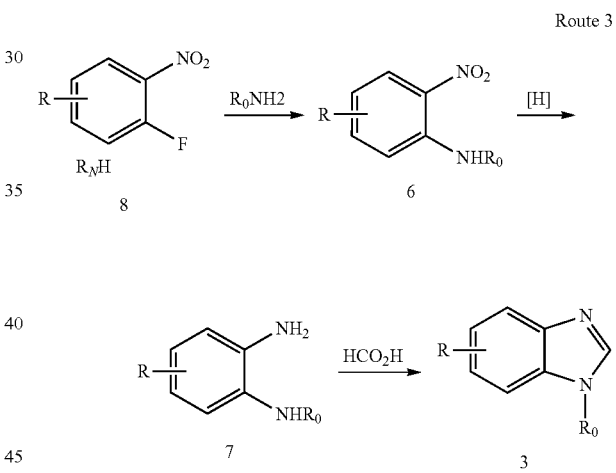

In general, the current synthetic routes are time consuming and labor intensive in some cases, requiring purifications of several intermediates, and separation and characterization of regioisomers.

SUMMARY

The present invention provides a benzimidazole compound, and a preparation method thereof in view of the deficiencies existing in the prior art. Various substituted benzimidazole compounds by a $S_N2$ reaction and a cyclization reaction. Namely, o-fluorinated aryl-N, N-dimethylformamidine and primary amine are subjected to a cyclization by a one-pot reaction, wherein a fluorine atom is substituted by an amino, and then dimethylamine is eliminated, thus forming the product.

The technical scheme of the present invention is as follows:

a benzimidazole compound, as shown in formula (I),

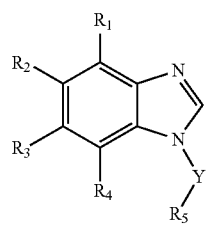

wherein, $R_1$ is H, —Cl, alkyl;
$R_2$ is —$NO_2$, —F, —Cl, Br, —$CF_3$, —CN, —$CO_2CH_3$, —$CO_2CH_3CH_2$;
$R_3$ is —H, alkyl, —CN, —$CF_3$;
$R_4$ is —H, —Cl, alkyl, cycloalkyl, —CN;
$R_5$ is —H, alkyl, fluoroalkyl, cycloalkyl, arylcyclo, heteroaryl ring;
Y is —CH, —$CH_2$, —N, —NH, —N, cycloalkyl.

A method for producing a benzimidazole compound of the present invention includes the following steps:
using a compound of formula (II) and a compound of formula (III), i.e., o-fluorinated aryl-N,N-dimethyl-formamidine and primary amine, as raw materials, and performing a reaction on the raw materials in a solvent to synthesizing a compound of formula (I), i.e., the benzimidazole compound; wherein the specific process is as follows:

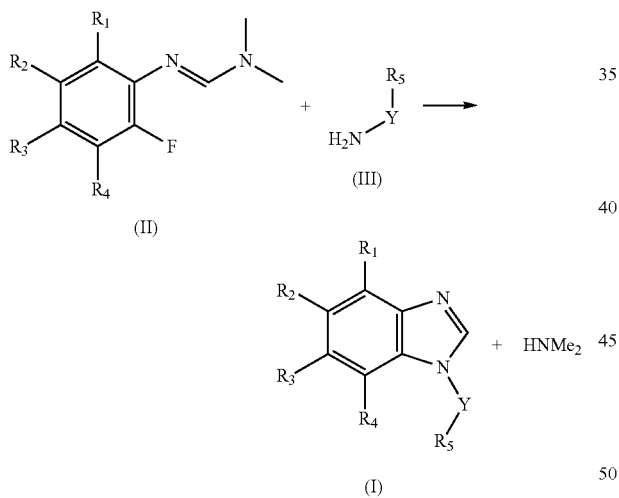

substituents $R_1$-$R_5$ and Y in the compound of the formula (II) and the compound of the formula (III) are the same as that in the compound of the formula (I).

Further, in the preparation method, a molar ratio of the compound of the formula (II) to the compound of the formula (III) is 1: 1-12.

Further, in the preparation method, in the compound of the formula (II), $R_2$ is an electron withdrawing group, and $R_2$ is preferably —$NO_2$, —$CF_3$ or —CN.

Further, in the preparation method, the compound of the formula (III) is a primary amine, preferably a fatty primary amine, an aromatic primary amine or a primary amine containing a heterocyclic ring.

Further, in the preparation method, the solvent is N,N-dimethylformamide (DMF), dimethyl acetamide (DMA), dimethyl sulfoxide (DMSO), hexamethylphosphoramide (HMPA), tetrahydrofuran (THF) or dioxane.

Further, in the preparation method, a reaction temperature is 80° C.-220° C., and reaction time is 0.2 h-5.0 h.

The advantages of the present invention are as follows: Various substituted benzimidazoles are synthesized by a $S_N2$ reaction and a cyclization reaction. Namely, o-fluorinated aryl-N,N-dimethyl-formamidine and primary amine are subjected to a cyclization by a one-pot reaction, wherein a fluorine atom is substituted by an amino, and then dimethylamine is eliminated, thus forming the product. Compared with the traditional method, the substitution and the cyclization are completed in one pot, the reaction process does not require the use of metal catalysts and/or toxic reagents, the synthesis method has specific selectivity, the reaction product has no isomers, and the process flow is simple and the yield is high.

DETAILED DESCRIPTION OF THE EMBODIMENTS

In order to better understand the contents of the present invention, the following embodiments are used to further explain the present invention.

In the present invention, unless otherwise specified, the room temperature is 25° C., the stirring method defined by the rotation speed is a conventional stirring method, and the rotation speed is 500-1000 rpm.

Embodiment 1

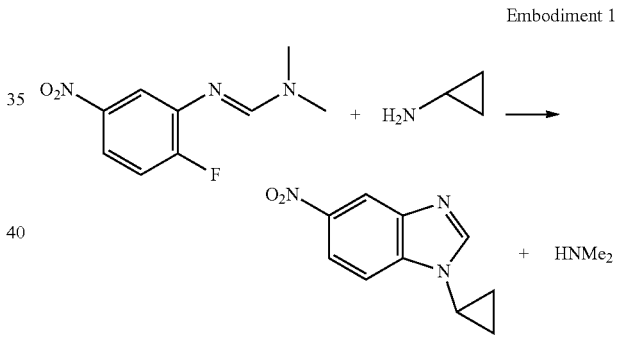

A magnetic stir bar, 15 mL of dimethyl sulfoxide (DMSO), 0.21 g (1 mmol) of (E)-N'-(2-fluoro-5-nitrophenyl)-N,—N-dimethylformamidine, and 0.285 g (5 mmol) of cyclopropylamine were added to a 25 mL single-neck round-bottom flask. An air condenser was placed on the one-neck round-bottom flask. The reaction flask was placed in an oil bath and heated to a temperature of 150° C., and the temperature was maintained for 2 h. After the reaction was stopped, the reaction flask was cooled to room temperature, and then a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to obtain a product of 1-cyclopropyl-5-nitro-1H-benzo[d]imidazole, a weight of the product was 0.115 g, and a yield of the product was 57%.

$^1$H NMR (500 MHz, MeOD) δ ppm 1.07-1.17 (m, 2H), 1.21-1.32 (m, 2H), 3.60 (dt, J=7.02, 3.51 Hz, 1H), 7.81-7.88 (m, 1H), 8.22-8.32 (m, 1H), 8.45 (s, 1H), 8.55 (br. s., 1H); $^{13}$C NMR (126 MHz, MeOD) ppm 5.32, 42.80, 11.31, 115.63, 118.80, 139.51, 142.57, 144.46, 148.01; HRMS calcd. for $C_{10}H_9N_3O_2$: 203.0695, found 203.0682.

Embodiment 2

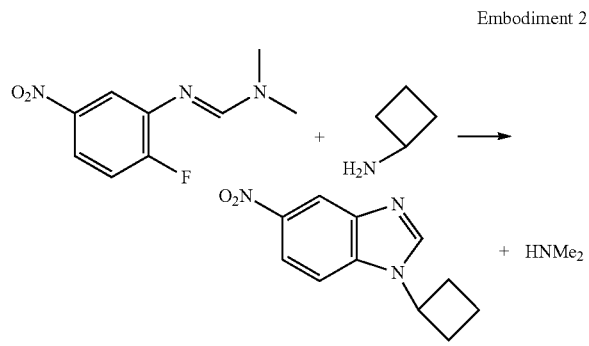

A magnetic stir bar, 15 mL of dimethyl sulfoxide (DMSO), 0.21 g (1 mmol) of (E)-N'-(2-fluoro-5-nitrophenyl)-N,—N-dimethylformamidine, and 0.355 g (5 mmol) of cyclobutylamine were added to a 25 mL single-neck round-bottom flask. An air condenser was placed on the one-neck round-bottom flask. The reaction flask was placed in an oil bath and heated to a temperature of 150° C., and the temperature was maintained for 2 h. After the reaction was stopped, the reaction flask was cooled to room temperature, and a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to form a product of 1-cyclobutyl-5-nitro-1H-benzo[d]imidazole, a weight of the product was 0.117 g, and a yield of the product was 54%.

$^1$H NMR (500 MHz, MeOD) δ ppm 1.94-2.15 (m, 2H), 2.51-2.73 (m, 4H), 4.98-5.10 (m, 1H), 7.72 (d, J=8.85 Hz, 1H), 8.20 (d, J=8.85 Hz, 1H), 8.54 (d, J=8.85 Hz, 2 H); $^{13}$C NMR (126 MHz, MeOD) δ ppm 15.12, 29.83, 47.50, 47.66, 47.84, 48.01, 48.18, 48.35, 48.52, 48.63, 48.66, 50.46, 111.27, 115.61, 118.50, 137.66, 142.76, 144.22, 145.75; HRMS calcd. for $C_{11}H_{11}N_3O_2$: 217.0851, found 217.0838.

Embodiment 3

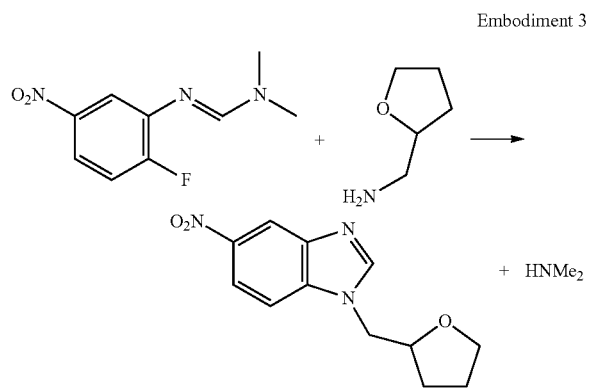

A magnetic stir bar, 15 mL of dimethyl sulfoxide (DMSO), 0.21 g (1 mmol) of (E)-N'-(2-fluoro-5-nitrophenyl)-N,—N-dimethylformamidine, and 0.505 g (5 mmol) of (tetrahydrofuran-2-yl)methanamine were added to a 25 mL single-neck round-bottom flask. An air condenser was placed on the one-neck round-bottom flask. The reaction flask was placed in an oil bath and heated to a temperature of 160° C., and the temperature was maintained for 3 h. After the reaction was stopped, the reaction flask was cooled to room temperature, and a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to form a product of 5-nitro-1-((tetrahydrofuran-2-yl)methyl)-1H-benzo[d]imidazole, a weight of the product was 0.192 g, and a yield of the product was 78%.

$^1$H NMR (500 MHz, MeOD) δ ppm 1.56-1.71 (m, 1H), 1.77-1.86 (m, 1H), 1.86-1.96 (m, 1H), 2.14 (ddd, J=7.78, 5.19, 5.04 Hz, 1H), 3.69-3.78 (m, 1H), 3.80-3.88 (m, 1H), 4.23-4.32 (m, 1H), 4.32-4.42 (m, 1H), 4.54 (dd, J=14.65, 2.75 Hz, 1H), 7.82 (d, J=8.85 Hz, 1H), 8.25 (dd, J=8.85, 2.14 Hz, 1H), 8.44 (s, 1H), 8.57 (d, J=2.14 Hz, 1H); $^{13}$C NMR (126 MHz, MeOD) δ ppm 25.66, 28.68, 49.19, 68.28, 77.80, 111.53, 115.42, 118.56, 138.75, 142.22, 144.09, 148.44; HRMS calcd. for $C_{12}H_{13}N_3O_3$: 247.0957, found 247.0942.

Embodiment 4

4-(3-(5-nitro-1H-benzo[d]imidazol-1-yl)morpholine

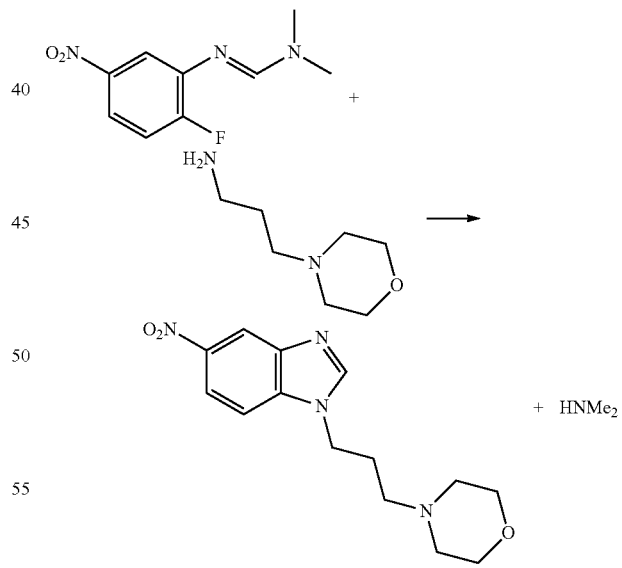

A magnetic stir bar, 15 mL of dimethyl acetamide (DMA), 0.21 g (1 mmol) of (E)-N'-(2-fluoro-5-nitrophenyl)-N,N-dimethylformamidine, and 1.0 g (7 mmol) of 3-morpholino-propan-1-amine were added to a 25 mL single-neck round-bottom flask. An air condenser was placed on the one-neck round-bottom flask. The reaction flask was placed in an oil bath and heated to a temperature of 160° C., and the temperature was maintained for 3 h. After the reaction was stopped, the reaction flask was cooled to room temperature, and a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to form a product of 4-(3-(5-nitro-1H-benzo[d]imidazol-1-yl)propyl) morpholine, a weight of the product was 0.246 g, and a yield of the product was 85%.

$^1$H NMR (500 MHz, MeOD) δ ppm 2.13 (t, J=6.71 Hz, 2H), 2.29-2.47 (m, 6H), 3.65 (t, 14.73 Hz, 4H), 4.48 (t, J=6.71 Hz, 2H), 7.83 (d, J=9.16 Hz, 1H), 8.28 (dd, J=8.85, 2.14 Hz, 1H), 8.49 (s, 1H), 8.60 (d, J=2.14 Hz, 1H); $^{13}$C NMR (126 MHz, MeOD) δ ppm 26.11, 43.38, 47.50, 47.67, 47.84, 48.01, 48.18, 48.35, 48.52, 53.60, 55.28, 66.77, 111.11, 115.58, 118.61, 138.35, 142.47, 144.15, 148.13; HRMS calcd. for $C_{14}H_{18}N_4O_3$: 290.1379, found 290.1381.

Embodiment 5

A magnetic stir bar, 15 mL of dimethyl acetamide (DMA), 0.225 g (1 mmol) of (E)-N'-(2-fluoro-4-methyl-5-nitrophenyl)-N,N-dimethylformamidine, and 1.0 g (7 mmol) of 3-morpholinopropan-1-amine were added to a 25 mL single-neck round-bottom flask. An air condenser was placed on the one-neck round-bottom flask. The reaction flask was placed in an oil bath and heated to a temperature of 170° C., and the temperature was maintained for 1 h. After the reaction was stopped, the reaction flask was cooled to room temperature, and a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to form a product of 4-(3-(6-methyl-5-nitro-1H-benzo[d]imidazol-1-yl) propyl) morpholine, a weight of the product was 0.216 g, and a yield of the product was 71%.

$^1$H NMR (400 MHz, MeOD) δ ppm 2.11 (t, J=6.65 Hz, 2H), 2.33 (t, J=6.78 Hz, 2H), 2.35-2.44 (m, 4H), 2.72 (s, 3H), 3.62-3.70 (m, 4H), 4.42 (t, J=6.78 Hz, 2H), 7.66 (s, 1H), 8.35 (s, 1H), 8.38 (s, 1H); $^{13}$C NMR (101 MHz, MeOD) δ ppm 19.83, 25.76, 42.76, 53.23, 54.86, 66.40, 113.04, 115.98, 128.43, 136.74, 140.44, 145.31, 147.20; HRMS calcd. for $C_{15}H_{20}N_4O_3$: 304.1535, found 304.1519.

Embodiment 6

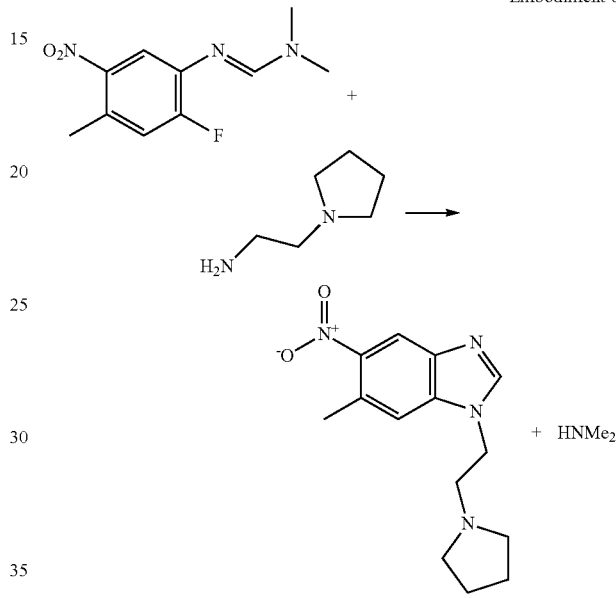

A magnetic stir bar, 15 mL of dimethyl acetamide (DMA), 0.225 g (1 mmol) of (E)-N'-(2-fluoro-4-methyl-5-nitrophenyl)-N,N-dimethylformamidine, and 0.799 g (7 mmol) of 2-(pyrrolidin-1-yl)ethanamine were added to a 25 mL single-neck round-bottom flask. An air condenser was placed on the one-neck round-bottom flask. The reaction flask was placed in an oil bath and heated to a temperature of 170° C., and the temperature was maintained for 1 h. After the reaction was stopped, the reaction flask was cooled to room temperature, and a reaction mixture was poured into a 250 mL separatory funnel containing 50 mL of water to form a mixed solution. Subsequently, the mixed solution was extracted with 30 mL of ethyl acetate. The extraction was repeated three times. Organic phases were collected, and then washed with saturated salt water and water successively, and dried overnight with anhydrous sodium sulfate. The ethyl acetate in organic phase was removed by a rotary evaporation. A mixture obtained after the rotary evaporation was separated by a silica gel column chromatography to form a product of 6-methyl-5-nitro-1-(2-(pyyrolidin-1-yl)ethyl)-1H-benzo[d]imidazole-1, a weight of the product was 0.120 g, and a yield of the product was 44%.

$^1$H NMR (500 MHz, MeOD) δ ppm 1.78 (br. s., 4H), 2.59 (br. s., 4H), 2.66 (s, 3H), 2.90-3.02 (m, 2H), 4.42 (t, J=6.71 Hz, 2H), 7.58 (s, 1H), 8.28 (s, 1H), 8.35 (s, 1H); 13C NMR (126 MHz, MeOD) δ ppm 20.18, 23.45, 44.30, 47.50, 47.68, 47.85, 48.02, 48.19, 48.36, 48.53, 54.11, 54.98, 113.25, 116.38, 128.90, 137.04, 140.86, 145.72, 147.55; HRMS calcd. for $C_{14}H_{15}N_4O_2$: 274.1430, found 274.1415.

Embodiment 7

6-methyl-5-nitro-1-(2-(pyrrolidin-1-yl)ethyl)-1H-benzo[d]imidazole

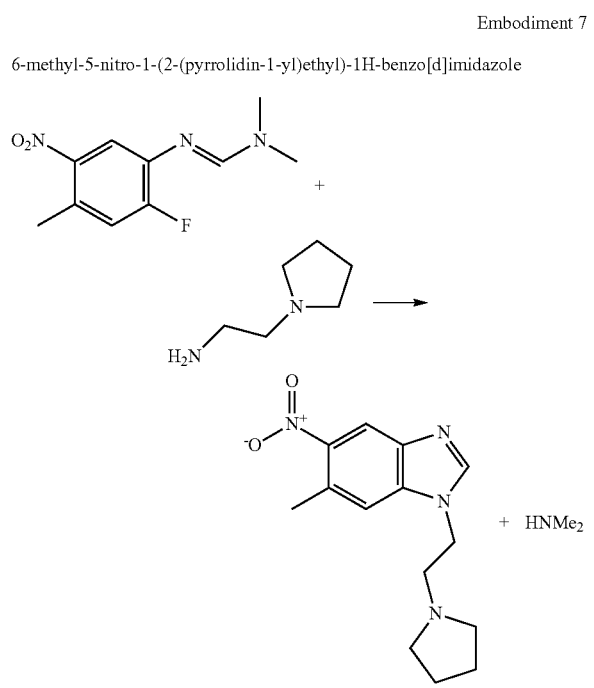
+ HNMe₂

A magnetic stir bar, 1.8 mL of dimethyl acetamide (DMA), 45 mg (0.2 mmol) of (E)-N'-(2-fluoro-4-methyl-5-nitrophenyl)-N,N-dimethylformamidine, and 0.799 g (7 mmol) of 2-(pyrrolidin-1-yl)ethanamine were added to a 2 mL Biotage microwave reaction tube. After capping, a reaction mixture was heated to a temperature of 160° C., and the temperature was maintained for 15 min in a Biotage microwave reactor. After the reaction was stopped, the reaction flask was cooled to room temperature, and the reaction mixture was poured into a 50 mL separatory funnel containing 10 mL of water to form a mixed solution. The mixed solution was extracted with 5 mL of ethyl acetate. The extraction was repeated three times. Organic phases were collected, and then washed with saturated salt water and water successively, and dried overnight with anhydrous sodium sulfate. The ethyl acetate in the organic phase was removed by a rotary evaporation, and a mixture obtained after the rotary evaporation was purified by a silica gel column chromatography to obtain a product of 6-methyl-5-nitro-1-(2-(pyrronlidin-1)ethyl)-1H-benzo[d]imidazole-1, a weight of the product was 0.120 g, and a yield of the product was 48%.

$^1$H NMR (500 MHz, MeOD) δ ppm 1.78 (br. s., 4H), 2.59 (br. s., 4H), 2.66 (s, 3H), 2.90-3.020 (m, 2H), 4.42 (t, J=6.71 Hz, 2H), 7.58 (s, 1H), 8.28 (s, 1H), 8.35 (s, 1H); $^{13}$CNMR (126 MHz, MeOD) δ ppm 20.18, 23.45, 44.30, 47.50, 47.68, 47.85, 48.02, 48.19, 48.36, 48.53, 54.11, 54.98, 113.25, 116.38, 128.90, 137.04, 140.86, 145.72, 147.55; HRMS calcd. for $C_{14}H_{18}N_4O_2$: 274.1430, found 274.1415.

What is claimed is:

1. A method for preparing a benzimidazole compound, comprising the following steps:
   using o-fluorinated aryl-N,N-dimethyl-formamidine having a compound of formula (II) and a primary amine having a compound of formula (III), as raw materials, and performing a reaction on the raw materials in a solvent to synthesize the benzimidazole compound; wherein a specific process is as follows:

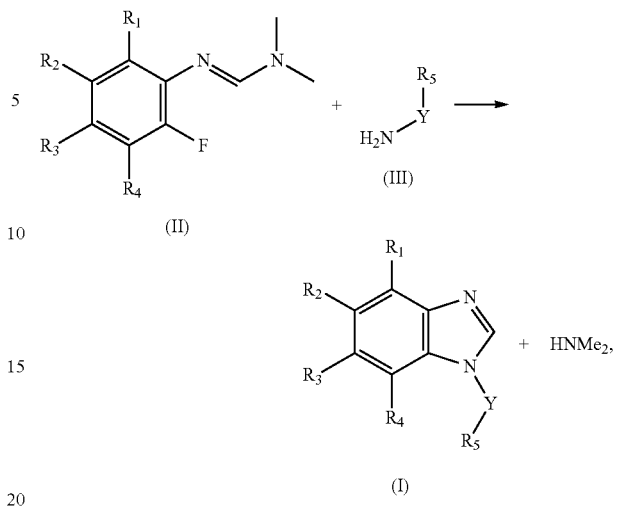

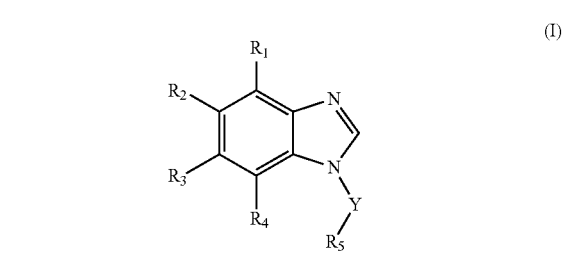

wherein the benzimidazole compound comprises the formula (I),

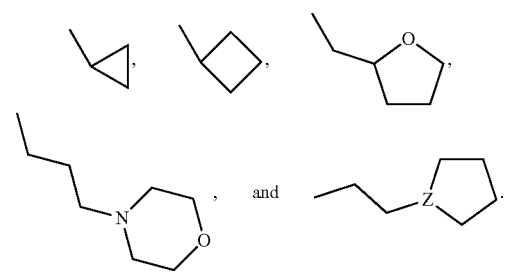

wherein $R_1$ is H, —Cl, or alkyl;

$R_2$ is —NO₂, —F, Br, —CF₃, —CN, —CO₂CH₃, or —CO₂CH₂CH₃;

$R_3$ is —H, alkyl, —CN, or —CF₃, $R_4$ is —H, —Cl, alkyl, cycloalkyl, or —CN;

—YR₅ is selected from the group consisting of

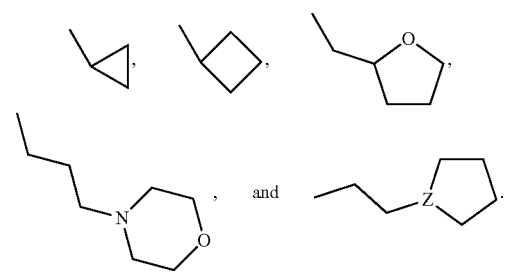

2. The method according to claim 1, wherein a molar ratio of the compound of the formula (II) to the compound of the formula (III) is 1: 1-12.

3. The method according to claim 1, wherein $R_2$ is —NO₂, —CF₃ or —CN.

4. The method according to claim 1, wherein the solvent is N,N-dimethylformamide (DMF), dimethyl acetamide (DMA), dimethyl sulfoxide (DMSO), hexamethylphosphoramide (HMPA), tetrahydrofuran (THF) or dioxane.

5. The method according to claim 1, wherein a reaction temperature is 80° C.-220° C., and a reaction time is 0.2 h-5.0 h.

\* \* \* \* \*

UNITED STATES PATENT AND TRADEMARK OFFICE
CERTIFICATE OF CORRECTION

| | | |
|---|---|---|
| PATENT NO. | : 10,787,420 B2 | |
| APPLICATION NO. | : 16/485457 | |
| DATED | : September 29, 2020 | |
| INVENTOR(S) | : Xuejing Liu, Ying Han and Liang Yang | |

It is certified that error appears in the above-identified patent and that said Letters Patent is hereby corrected as shown below:

On the Title Page

The (72) Inventors should read Xuejing Liu, Zaozhuang (CN); Ying Han, Suzhou (CN); Liang Yang, Zaozhuang (CN)

Signed and Sealed this
Twenty-fourth Day of November, 2020

Andrei Iancu
*Director of the United States Patent and Trademark Office*